(12) United States Patent
Bono et al.

(10) Patent No.: US 11,523,833 B2
(45) Date of Patent: Dec. 13, 2022

(54) SURGICAL ROTARY TOOL

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US)

(73) Assignee: Globus Medical, Inc., Audubon, PA (US)

( * ) Notice: Subject to any disclaimer, the term of this patent is extended or adjusted under 35 U.S.C. 154(b) by 5 days.

(21) Appl. No.: 15/932,361

(22) Filed: Feb. 16, 2018

(65) Prior Publication Data

US 2018/0263637 A1 Sep. 20, 2018

Related U.S. Application Data

(60) Provisional application No. 62/460,481, filed on Feb. 17, 2017.

(51) Int. Cl.
| | |
|---|---|
| *A61B 17/16* | (2006.01) |
| *A61B 17/32* | (2006.01) |
| *A61B 17/00* | (2006.01) |
| *A61B 50/30* | (2016.01) |
| *A61B 90/94* | (2016.01) |

(52) U.S. Cl.
CPC ...... *A61B 17/1617* (2013.01); *A61B 17/1622* (2013.01); *A61B 17/1624* (2013.01); *A61B 17/1631* (2013.01); *A61B 17/1628* (2013.01); *A61B 17/1633* (2013.01); *A61B 17/32002* (2013.01); *A61B 50/30* (2016.02); *A61B 90/94* (2016.02); *A61B 2017/0023* (2013.01); *A61B 2017/1602* (2013.01)

(58) Field of Classification Search
CPC ............ A61B 17/1617; A61B 17/1624; A61B 17/1631; A61B 2017/320758; A61B 2017/320016; A61B 17/32002; A61B 17/1633; A61B 17/16; A61B 17/1613
USPC ........................................................ 606/180
See application file for complete search history.

(56) References Cited

U.S. PATENT DOCUMENTS

| | | | | |
|---|---|---|---|---|
| 4,646,738 | A * | 3/1987 | Trott ................ | A61B 17/32002 600/565 |
| 5,591,170 | A * | 1/1997 | Spievack ............. | A61B 17/151 30/122 |
| 5,735,535 | A * | 4/1998 | McCombs ........... | A61B 17/162 279/131 |
| 5,993,454 | A * | 11/1999 | Longo ................ | A61B 17/1624 606/80 |
| 7,066,940 | B2 * | 6/2006 | Riedel ................. | A61B 17/162 606/167 |
| 2003/0163134 | A1 * | 8/2003 | Riedel ................. | A61B 17/162 606/79 |
| 2007/0244825 | A1 * | 10/2007 | Semmer ................ | G06F 21/123 705/59 |

(Continued)

OTHER PUBLICATIONS

Definition of Integral. Printed Aug. 14, 2019 (Year: 2019).*

*Primary Examiner* — Tan-Uyen T Ho
*Assistant Examiner* — Bridget E. Rabaglia (57) ABSTRACT

A rotary surgical tool is provided and has an effector or cutter that is usable to remove or otherwise modify tissue such as bone. The tool includes a motor coupled to the effector with a single piece shaft that is integral with the effector and also serves as the motor output shaft.

9 Claims, 8 Drawing Sheets

(56) References Cited

U.S. PATENT DOCUMENTS

| | | | | |
|---|---|---|---|---|
| 2009/0264893 | A1* | 10/2009 | Beale | A61B 17/7091 606/99 |
| 2009/0326537 | A1* | 12/2009 | Anderson | A61B 17/17 606/80 |
| 2011/0245833 | A1* | 10/2011 | Anderson | A61B 17/1626 606/80 |
| 2011/0301611 | A1* | 12/2011 | Garcia | A61B 17/162 606/80 |
| 2012/0239008 | A1* | 9/2012 | Fojtik | A61B 17/320758 606/1 |
| 2013/0060278 | A1* | 3/2013 | Bozung | A61B 17/1746 606/205 |
| 2014/0251845 | A1* | 9/2014 | Roesler | B65D 77/02 206/363 |
| 2014/0262408 | A1* | 9/2014 | Woodard | A61B 17/1624 173/216 |
| 2014/0305988 | A1* | 10/2014 | Boudreaux | A61B 17/0686 227/175.3 |
| 2015/0233757 | A1* | 8/2015 | Ebner | G01H 1/00 73/649 |
| 2016/0120553 | A1* | 5/2016 | Xie | A61B 17/162 606/80 |
| 2016/0128704 | A1* | 5/2016 | McGinley | A61B 17/1637 606/80 |
| 2017/0020536 | A1* | 1/2017 | Johnson | A61B 17/164 |
| 2017/0150975 | A1* | 6/2017 | Bozung | A61B 17/1622 |
| 2018/0250020 | A1* | 9/2018 | Carusillo | A61B 90/06 |

* cited by examiner

SURGICAL ROTARY TOOL

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/460,481, entitled "SURGICAL ROTARY TOOL", filed Feb. 17, 2017. The content of the above referenced application is incorporated herein by reference.

FIELD OF THE INVENTION

The present invention relates to a rotary handheld surgical tool usable for cutting, drilling and grinding.

BACKGROUND OF THE INVENTION

Powered rotary tools for surgery are well known in the art. Many surgeons consider them indispensable for certain surgical procedures such as drilling, cutting and grinding. They are used to modify tissue, such as bone, at the surgical site so that the surgical procedure can be effected. Such a tool typically includes a tool head, or effector, that is rotated by an externally powered motor, such as an electrical motor. The tool head is part of an elongate shaft that is operably coupled to the rotor of the motor. The rotor of the motor effects rotation of the tool head and its shaft. The rotating tool head is used to effect some surgical operation, for example drilling, cutting and grinding. An actuator is provided to selectively effect powering of the motor rotor to effect rotation of the effector.

Such tools are expensive and, because of the numerous parts, difficult and expensive to sterilize for reuse, often requiring partial or complete disassembly. Also, the tools have separable parts, such as the tool head, that could become separated during use.

DESCRIPTION OF THE PRIOR ART

Examples of such rotary tools include those disclosed in U.S. Pat. Nos. 4,646,738; 5,735,535; 7,066,940; and U.S. Publication 2014/0,246,047. U.S. Pat. No. 4,646,738 is an electric motor powered tool that is quite complex, and it would require disassembly after use for sterilization. U.S. Pat. No. 5,735,535 is an electric motor powered tool that is also complex, would require disassembly after use for sterilization, and uses a chuck to hold the tool head. U.S. Pat. No. 7,066,940 is also an electrically powered tool that, like the last two mentioned tools, is complex, requires disassembly for sterilization, and has a separable cutting tool head. U.S. Patent Application Publication 2014/0246047 illustrates a different type of powered surgical tool, but it is not structured for using a rotary cutting tool. Like the aforementioned tools, it would require disassembly for sterilization and is quite complex in structure.

As can be seen from these mentioned surgical tools, even though advancements have been made over the years, no one has provided a simpler surgical tool that provides an advance in the art of rotary surgical tools that simplifies their use.

SUMMARY OF THE INVENTION

The present invention relates to a powered surgical tool that selectively rotates a tool head (effector) to effect tissue modification during a surgical procedure. The tool is adapted for disposal after use, as the tool's simple construction effects reduced cost without affecting its performance. The surgical tool includes a motor with a rotor having a support shaft. The effector is an integral part of the motor shaft, and the axes of rotation of the motor and the tool head are coaxial. A portion of the motor shaft carrying the tool head is enclosed in a shroud that, at the distal end adjacent the cutter head, provides for support of the distal end of the shaft. The tool is provided with a handle portion adapted for gripping by a surgeon, or surgeon's assistant, to effect operation of the surgical tool. The tool can be stored in packaging with indicia thereon indicating the type of tool and, in particular, the type of tool head on the tool contained in the package.

Accordingly, it is a primary objective of the instant invention to provide a rotary surgical tool that has a dedicated tool head integral with a motor shaft.

It is a further objective of the instant invention to provide such a rotary surgical tool that is simple in construction for reduced costs, allowing for its disposal after use.

It is yet another objective of the instant invention to provide such a rotary tool with a handle configured for controlling operation of the tool and its tool head.

It is a still further objective of the invention to provide such a rotary tool having a shroud surrounding the shaft portion on which the tool head is attached to provide stabilization and support for that shaft portion and tool head.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

Figure 1:
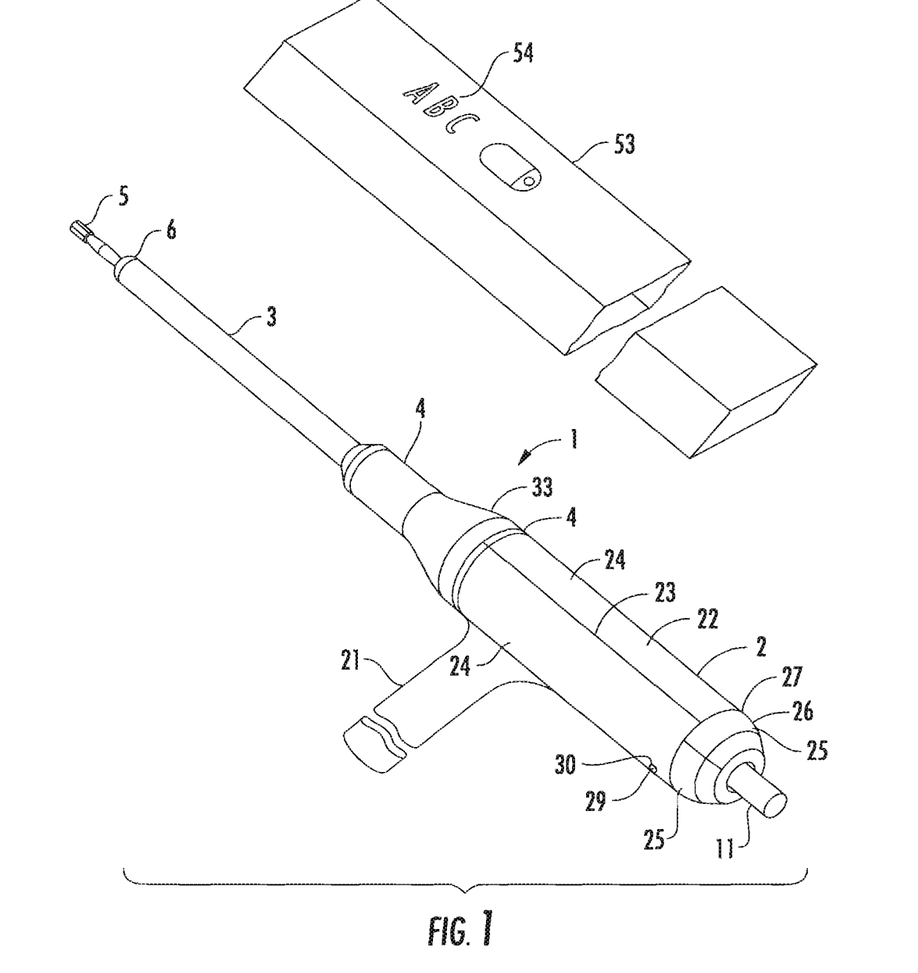
FIG. 1 is a perspective view of a powered surgical rotary tool with package.

The reference numeral 1 (FIG. 1) designates, generally, a rotary surgical tool having a hand grip portion 2 and a shroud extension 3 extending from the front end 4 of the grip 2. The tool 1 also includes a tool head or effector 5 at its distal end adjacent a distal end 6 of the shroud 3. The tool 1 includes a motor 10 mounted in the grip 2 (FIG. 2), and is operably connected to the tool head 5 for effecting selective powered rotation thereof. The motor 10 is suitably powered, such as with electricity or compressed air, and, as shown, is electrically powered via electricity from a power cord 11 operably connected to the motor 10. An actuator 12, such as a switch device electrically connected to the power cord 11 and motor 10, is provided to selectively couple the motor to an energy source and provide energy to the motor 10 to effect powered rotation thereof. The actuator 12 may also be constructed to provide for a single speed or a variable speed, and for selective locking in the "on" position.

The grip 2, in the illustrated structure, provides an in-line grip structure relative to the axis of rotation of the motor 10. However, it is to be noted that the grip 2 can have an auxiliary handle portion 21 (FIG. 1) at any suitable angle relative to the axis of rotation of the motor 10, for example, an approximate right angle. Any other suitable angle can be provided. In the illustrated structure, the actuator 12 is in the form of an electrical switch mounted on the grip 2 in a position suitable for easy operation by the user of the tool 1. In the case of a grip 2 that has a non-in-line user handle portion 21, the actuator 12 can be positioned on that handle portion for ease of access and operation.

The motor 10 has a rotor 14 that is rotatably mounted in the grip 2 and is enclosed therein, preferably in a substantially sealed manner, precluding the ingress of debris, fluids and tissue thereinto during storage and/or operation. The rotor 14 has a shaft with two end portions, a forward (or output) portion 15 and a rear (or support) portion 16, secured thereto and preferably permanently attached to the rotor. The attachment can be by press fitting the shaft portions 15, 16 into a bore in the rotor, adhesive securement, welding and the like. As shown, the shaft portions 15, 16 are part of a single piece shaft. The securement in essence makes the shaft portions 15, 16 an integral part of the rotor 14, forming a unitary assembly. The effector 5 is integral with the shaft forward portion 15. The shaft portions 15, 16 are each suitably mounted for rotation in respective bearings 18, 17. The bearings 17, 18 are suitably mounted within the grip 2. In the event the motor 10 is an electric motor, it also includes a stator 20. The motor 10 is preferably of a brushless type, and is operably connected to a motor controller 13. The stator 20 is suitably mounted within the grip 2, and is fixed against rotation relative to the grip 2. The motor 10 is electrically connected to the power cord 11 with the actuator 12 being electrically connected between the motor 10 and the power cord 11 to effect selective energizing of the controller 13 and motor 10, and hence its rotation. While an externally powered construction is shown utilizing a power cord 11, it is to be understood that the tool 1 can be powered by batteries or some other electricity storage device.

In the illustrated structure, the grip 2 is comprised of a motor housing portion 22 that is shown as comprising two halves 24 joined together along the separation line 23. Clips (not shown) can be provided to secure the halves 24 in a simple and secure manner. A grip butt 26 is shown as secured to the rear end 27 of the grip 2 and provides an access opening for a source of energy, such as the electric cord 11 or a compressed air hose. The butt 26, as shown, comprises two halves 25, allowing for mounting on the cord 11 therein and to the grip 2. In the illustrated embodiment, the butt 26 is mounted to the housing 22 in a snap together manner, and is retained in place as, for example, with one or more pins 29 extending into respective openings (or apertures) 30 through the housing 22.

Figure 2:
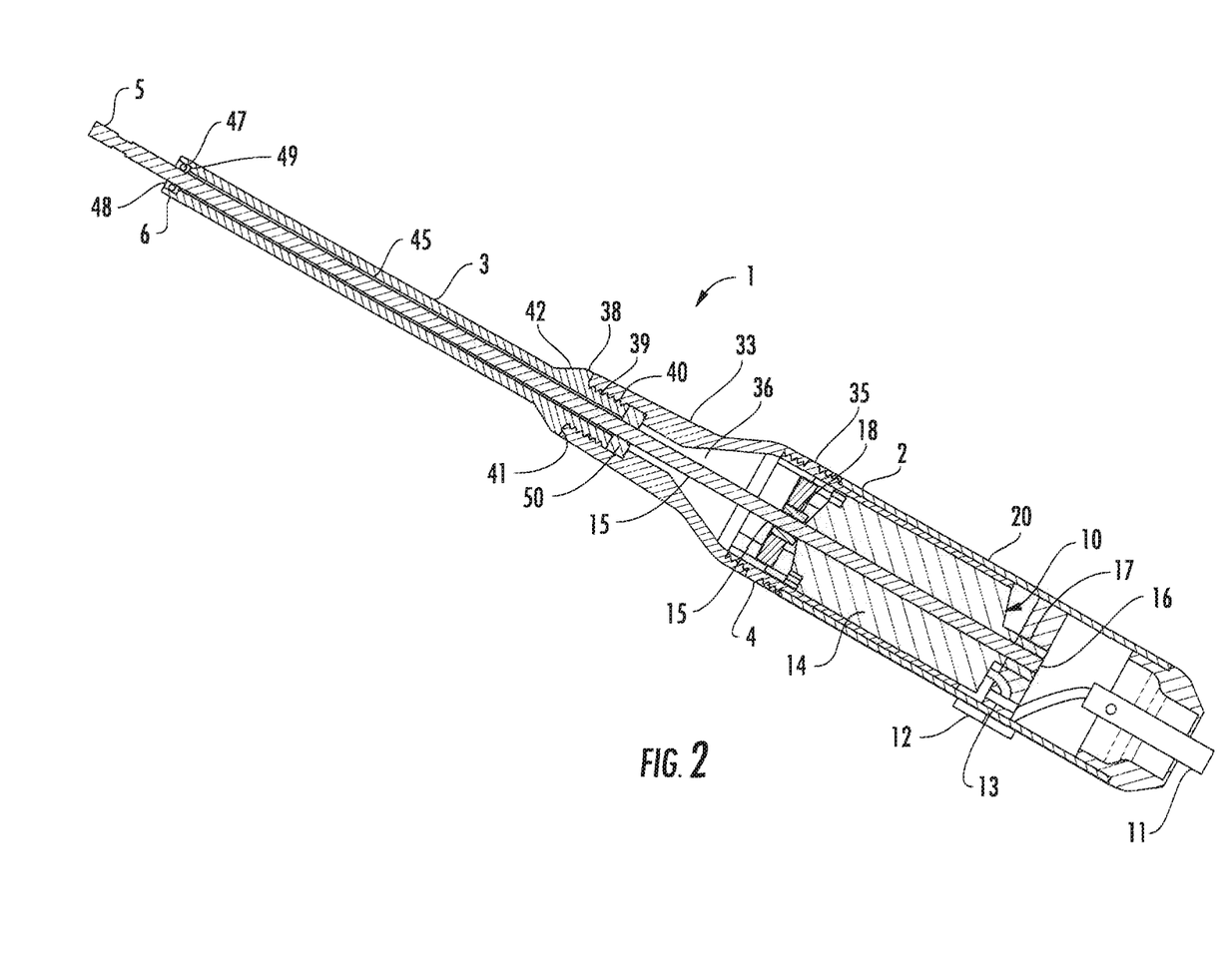
FIG. 2 is a perspective view of the surgical tool of FIG. 1, shown in cross-section to illustrate the internal details of the tool.
Figure 3:
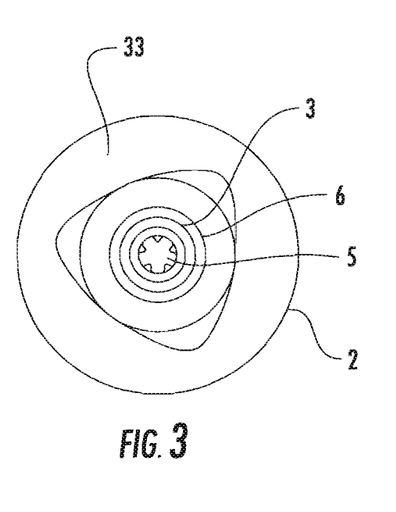
FIG. 3 is an end view of the tool of FIG. 1.

As best seen in FIG. 2, the grip 2 includes a nose 33 secured to the forward end 4 of the housing 22. In the illustrated structure, the nose 33 is suitably mounted to the housing 22, as with a threaded coupler 35. As shown, the coupler 35 has opposite ends thereof with male threads threadably engaged with female threaded portions of the housing 22 and the nose 33. The direction of the threading on the coupler 35 is preferably such as to provide for tightening under the influence of the torque induced in the nose 33 by rotation of the motor 10 and its shaft portion 15. The nose 33 has a through bore 36 for receipt of the shaft portion 15 therein.

As best seen in FIG. 2, the shroud 3 is secured to the nose 33 in a suitable and preferably separable manner. In the illustrated embodiment, the proximal end 38 of the shroud 3 is provided with a male threaded portion 39 that is in threaded engagement with a female threaded portion 40 of the nose 33. The direction of the threads on the male and female threaded portions 39, 40 is preferably such as to induce tightening of the threaded engagement from the torque applied to the shroud 3 during rotation of the motor 10 and its shaft portion 15 extending into the shroud 3. As shown, a shoulder 41 engages the free end of the nose 33 to limit how far the shroud 3 can be threaded into the nose 33. The shoulder 41 is at the proximal end of a frustoconical section 42 located at the proximal end 38 of the shroud 3. As shown, the nose 33 is of a single piece unitary construction. The shroud 3 is also preferably of a single piece unitary construction.

The shroud 3 has an elongate axial extending through bore 45 extending between its proximal end 38 and its distal end 6. The shaft portion 15 extends from the rotor 14 through the axial bore 45 and past the distal end 6. This positions the tool head 5 on the exterior of the shroud 3 for contact with tissue, such as skeletal components like bone and cartilage, or other forms of tissue, at a surgical site. In the illustrated embodiment, the shroud 3 has a bearing 47 positioned adjacent the end of the bore 45 which receives the shaft portion 15 therethrough to provide lateral support for the shaft portion 15. Preferably, the effector 5 has a cross sectional size and shape that will allow it to pass through the bearing 47 for assembly of the tool 1. The bearing 47 is mounted in a recess 48 that forms a stop shoulder 49 to limit movement of the bearing 47 into the shroud 3. The bearing 47 can be any suitable bearing, and can be made of a so-called self lubricating polymer; it could also be a ball bearing that is preferably sealed. The bearing 47 can be a single piece bearing when the tool head 5 is small enough to be inserted therethrough. The bearing 47 can also be a multiple piece bearing that can be mounted in the shroud 3 and attached thereto, as with mechanical locking elements or a suitable adhesive. An intermediate bearing 50 can be mounted in the shroud 3 or nose 33 with the shaft portion 15 extending therethrough and rotatably mounted therein. The bearings 47, 50 can be ball or roller bearings, and are preferably of a sealed type. It is to be understood that, for a tool configuration using a short shroud 3, the rigidity of the shaft portion is adequate to resist excessive bending during use, and that the bearings 47, 50 could be dispensed with. The shroud 3 and grip 2 can be made of any suitable material, such as a polymeric material or a metallic material such as stainless steel.

The effector 5 can be any suitable tool, such as a cutting burr (of an end and/or side cutting style), drill, polisher or the like, and is integral with the shaft portion 15. The tool head can be made from carbide or hardened corrosion resistant steel. It can be formed as part of the shaft portion 15, or formed separately and then permanently attached to the shaft portion 15 to be integral therewith.

In the illustrated embodiment, the motor 10, shaft portions 15, 16, axial bore 45, and the axis of rotation of the motor 10 shaft portions 15, 16 and effector 5 are coaxial. Also, the shaft portions 15, 16 are integral with the motor 10. The integral nature can be by press fitting the shaft portions 15, 16 into one or more bores in the motor 10. The shaft portion 15 is an integral structure from the motor 10 to the effector 5. The effector 5 is also integral with the shaft portion 15. The integral structure can be via joinder of the effector 5 to the shaft portion 15, as by welding in the event that the shaft portion 15 and effector 5 are made of metallic materials suitable for welding. The effector 5 and shaft portion 15 can also be formed as a unitary integral structure, as by machining from a single piece of material.

The tool 1 is packaged in a package 53 (see FIG. 1) to help ensure sterility, as is known in the art. The package 53 of the present invention also includes indicia 54 that disclose the type of tool head 5 on the tool 1. Preferably, the indicia 54 illustrate an enlarged view of the tool head 5, and can also provide a word description of the type of tool head 5.

Figure 4:
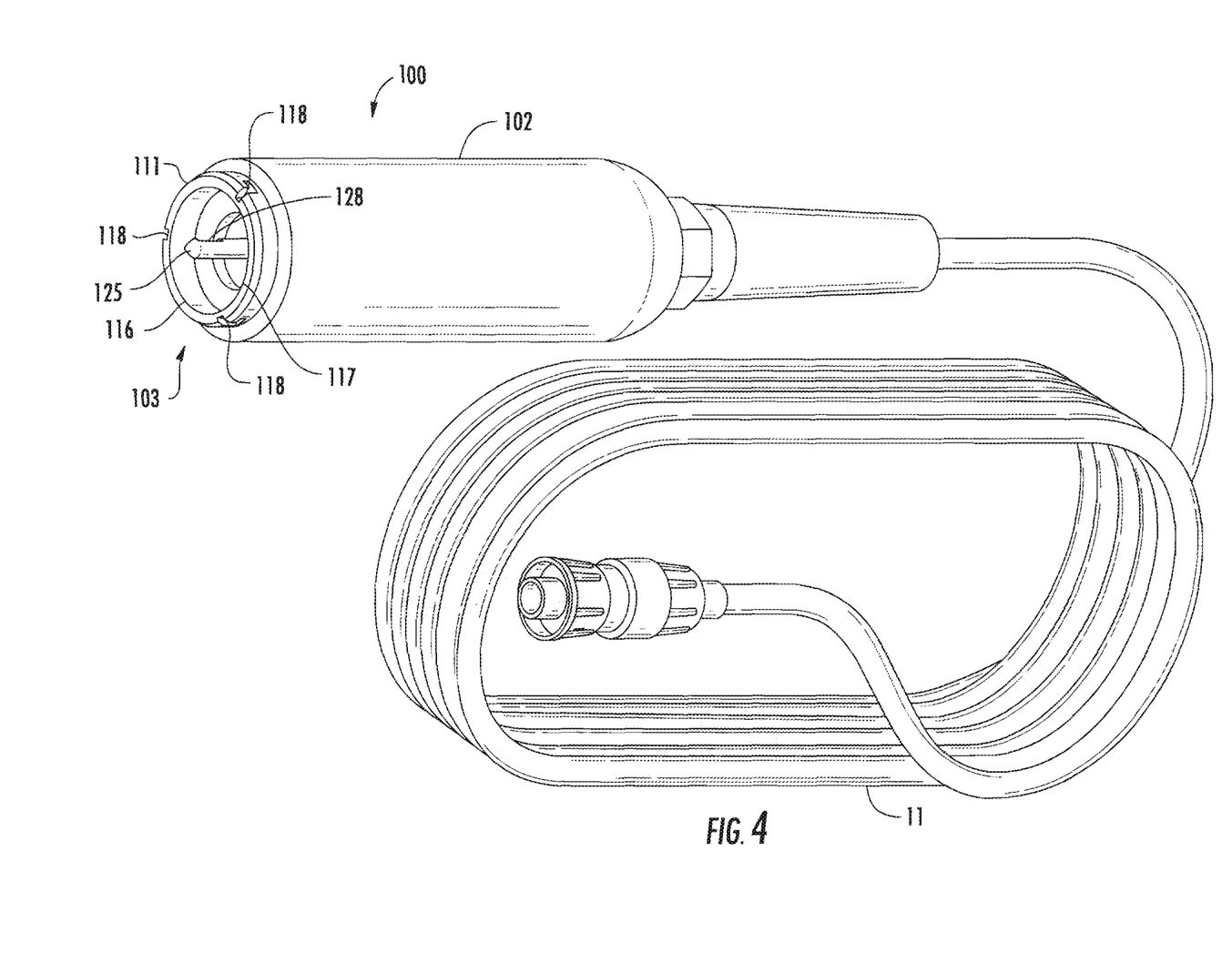
FIG. 4 is a perspective view of a motor housing/hand grip of an additional embodiment of the present invention.
Figure 5:
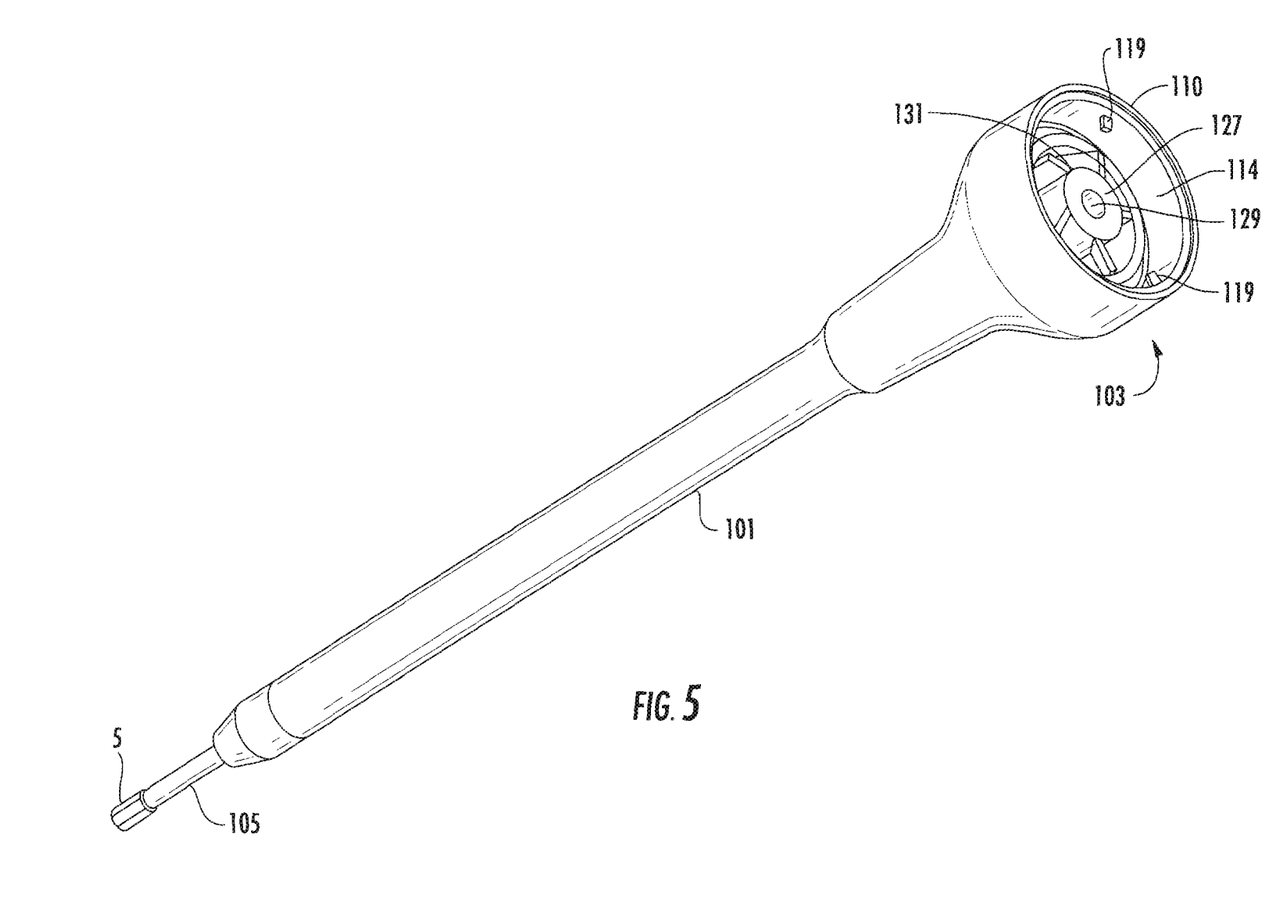
FIG. 5 is a perspective view of a shroud extension that is attachable to the motor housing of FIG. 4.
Figure 6:
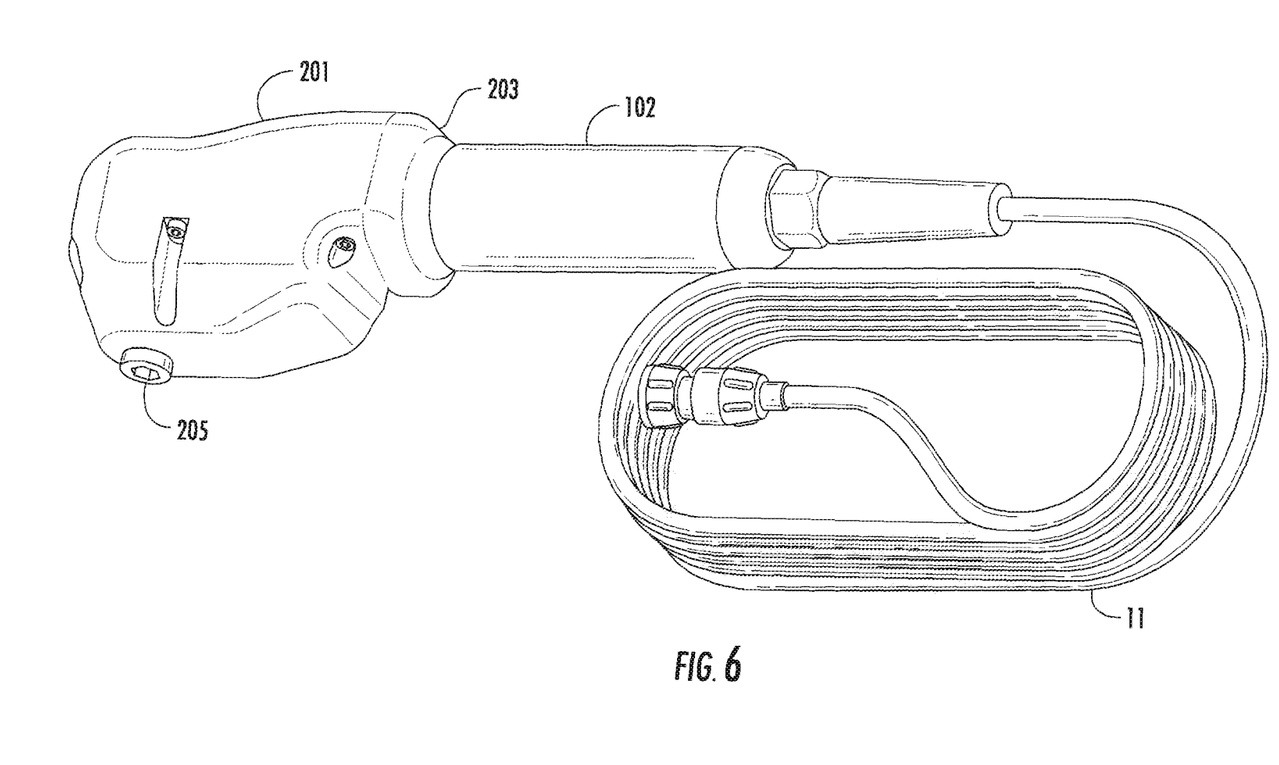
FIG. 6 is a perspective view of a right-angle drive attached to the motor housing of FIG. 4.
Figure 7:
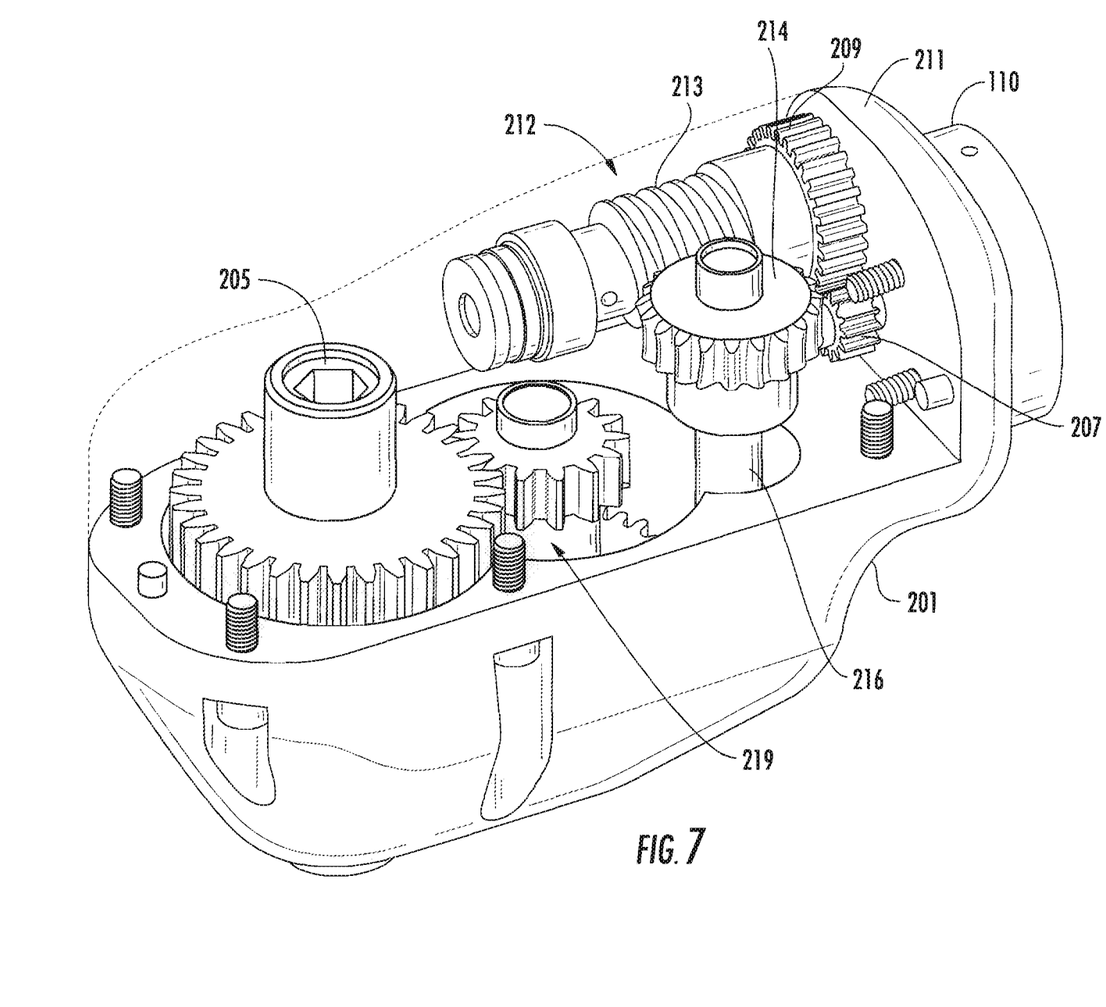
FIG. 7 is a fragmentary perspective view of the right-angle drive of FIG. 6, showing internal details.
Figure 8:
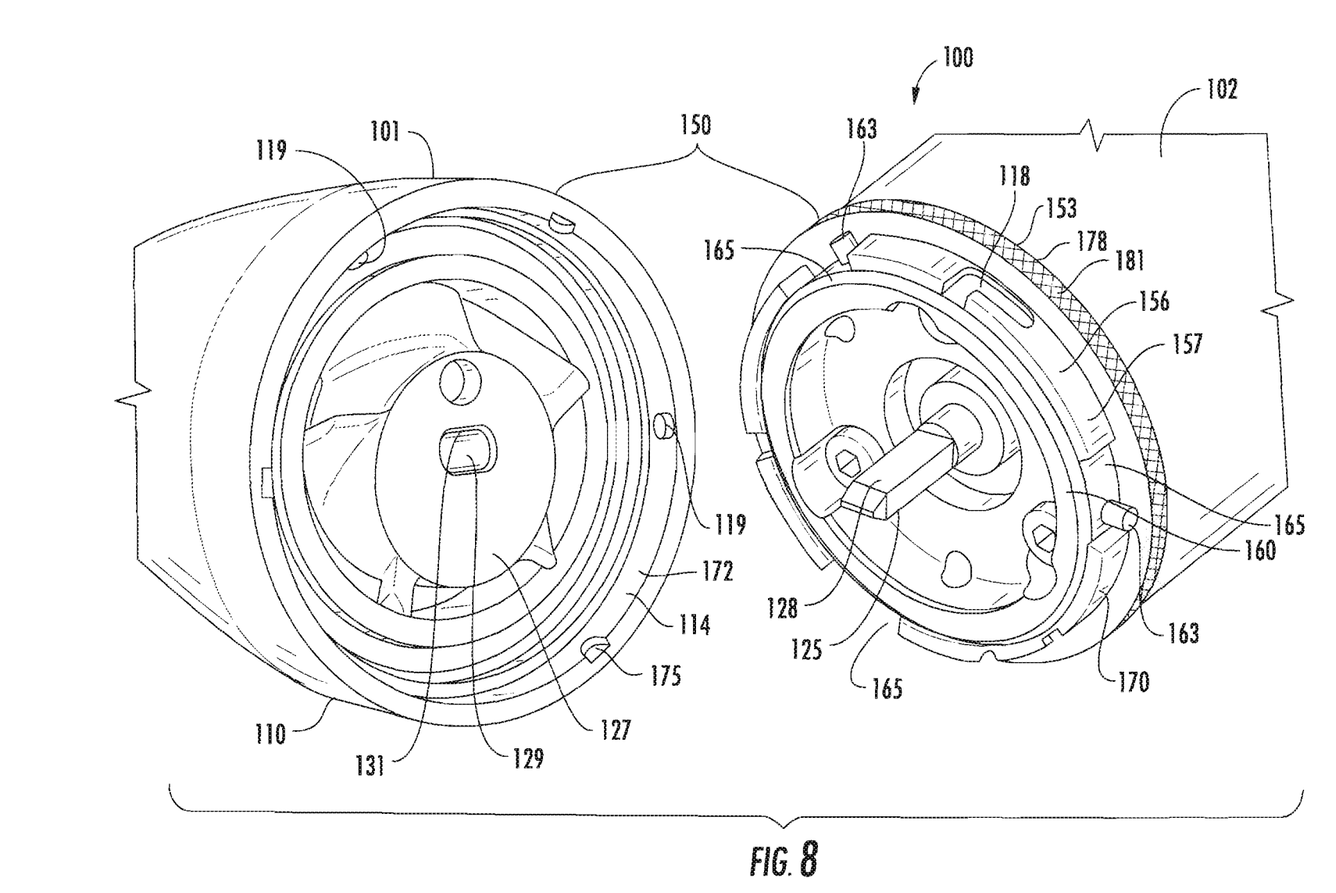
FIG. 8 is a perspective view of a second form of bayonet mount between the motor housing and shroud extension shown in FIGS. 4, 5.

FIGS. 4-8 show an additional embodiment of a tool 100 similar to the tool 1 described above. This embodiment of the present invention utilizes a bayonet mount for the tool 100 to removably secure a shroud extension 101 (like shroud 3 as described above) and a hand grip portion 102 (like hand grip portion 2 described above). The hand grip 102 houses a motor 10 (not shown but described above). The shroud extension 101 rotatably carries an effector 5 mounted to a shaft 105, and the effector is preferably integral with the shaft as described above. The motor 10 is operably coupled to the shaft 105 to effect its selective rotation. The motor 10 receives energy via an energy conductor 11 like an electric cord or compressed air hose, also as described above. The shroud 101 and hand grip (motor housing) 102 are releasably coupled to one another with a first bayonet mount, designated generally 103 as seen in FIGS. 4, 5, and a second bayonet mount designated generally 150 as seen in FIG. 8.

The bayonet mount of FIGS. 4, 5 includes a female portion 110 and a male portion 111. The female portion 110 is shown on the shroud extension, and the male portion 111 is shown on the hand grip 102. It is to be understood that this arrangement can be reversed. The female portion 110 has a cylindrical hollow sleeve 114 that is sized and shaped to rotatably receive a cylindrical collar 116 therein. The outer cylindrical surface 117 of the collar 116 has a plurality of generally L shaped recesses 118 therein and circumferentially spaced apart. Each recess 118 is adapted to receive a respective retainer pin 119 therein upon axial movement of the sleeve 114, followed by relative rotational movement onto the collar 116, releasably locking the shroud extension 101 to the hand grip 102.

One embodiment of the tool 100 utilizes the unitary shaft and motor construction described above. Additionally, the tool 100 can utilize a shaft 105 that is not integral with the motor 10, as seen in FIGS. 4, 5. In this embodiment, the motor (not shown, but like motor 10 described above) has an output shaft portion 125 that is coupled to the motor 10 and drivingly engages a driven coupler member 127 that is operably connected to the shaft 105. As shown, the shaft portion 125 has at least one key surface 128, which is shown as being generally flat. The shaft 125 is received in a bore 129 which also has a key surface 131 which mates with the key surface 128 so that the shaft portion 125 will positively drive the shaft 105 while permitting easy coupling of the shaft portion 125 to the shaft 105. Coupling is effected by longitudinal movement of the shaft portion 125 into the bore 129.

FIG. 8 illustrates another form of bayonet mount, designated generally 150, releasably coupling the hand grip 102 to the shroud extension 101. As shown, the shroud extension 101 has a female portion 110 that couples to a male portion 153 The shroud extension 101 has a driven member 127 connected to the shaft 105. A shaft portion 125 has at least one key surface 128, which is shown as being generally flat. The shaft 125 is received in a bore 129 which also has a key surface 131 that mates with the key surface 128 so that the shaft portion 125 will positively drive shaft 105 while permitting easy coupling of the shaft portion 125 to the shaft 105. The female portion 110 has a cylindrical hollow sleeve 114 that is sized and shaped to rotatably receive a cylindrical collar 156 therein. The outer cylindrical surface 157 of the collar 156 has a plurality of generally L shaped recesses 118 therein and circumferentially spaced apart. Each recess 118 is adapted to receive a respective retainer pin 119 therein upon axial movement of the sleeve 114, followed by relative rotational movement of the collar 156, releasably locking the shroud extension 101 to the hand grip 102. As shown, the male portion 153 is rotatably mounted on the hand grip 102. As shown, the male portion 153 is rotatably mounted on a cylindrical sleeve 160 and is held against longitudinal movement on the hand grip 102 by pins 163, each received in a circumferentially extending slot 165. The sleeve 114 is provided with a plurality of pins 119 that project radially inwardly from the inner surface of the sleeve 114. Each of the pins 119 is received in a respective recess 118 and, upon first axial movement of the sleeve 114 relative to the male portion 153 followed by rotational movement of the collar 156 relative to the sleeve 114, the shroud extension 101 is releasably coupled to the hand grip 102. The pins 163 project outwardly from the surface 170 in which the recesses 118 are positioned. The surface 170 mates with the internal surface 172 of the sleeve 114. The surface 172 is provided with a plurality of recessed notches 175 each positioned and sized to receive a respective portion of a pin 163 therein to prevent relative rotation between the shroud extension 101 and the hand grip 102. The male portion 153 can then be rotated relative to the hand grip 102 to effect a mounting of the shroud extension 101 to the hand grip 102. As shown, the male portion 153 includes a flange 178 projecting radially outwardly from surface 170 of the collar 156. The flange 178 has an outer exposed surface 181 that is knurled to assist a user in rotating the male portion 153 on tine sleeve 160 to move the pins 119 into.

FIGS. 6, 7 illustrate a still further embodiment of the present invention that uses a bayonet mount to secure a handgrip 102, as described above, to a shroud extension 201. The bayonet mount 203 can be similar to those shown and FIGS. 4, 5 and 8. The details of the bayonet mount 203 are not shown in FIGS. 6, 7, but are shown in FIGS. 4, 5 and 8. The shroud extension 201 is shown in detail in FIG. 7. In this embodiment, the shroud extension 201 includes a right angle gear arrangement to effect rotation of an output drive 205 which would have a surgical tool, such as an effector 5, on a shaft (not shown). A motor output shaft portion (not shown, but like the output shaft portion 125 is coupled to a gear 207 which engages a mating gear 209 to effect its rotation. The gear 209 is rotatably mounted to a housing 211 via a bearing (not shown). The gear 209 drives a worm drive, designated generally 212, which includes a worm 213 and a worm gear 214 that drives a shaft 216 at a right angle to the shaft portion 125. The shaft 216 drives a gear arrangement comprising a series of rotatably mounted gears, designated generally 219, which provide a gear ratio to effect rotation of the output drive 205 at the desired rotational speed. The various shafts for the worm drive 212 and a gear arrangement 219 are suitably mounted on respective bearings (not shown). The output drive 205 can be suitably configured for receipt of a shaft 105 therein and prevent relative rotation between the shaft 105 and the output drive 205.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A rotary surgical tool comprising:
   a grip adapted for holding with a hand;
   a motor mounted in the grip, the motor including a rotor mounted for rotation in the motor upon an output shaft, said output shaft extending through said rotor to rotatably support said rotor and rotatable with said rotor and having a distal forward end spaced from the rotor, a shroud carried by said grip and surrounding a forward end portion of said output shaft, and including at least one bearing mounted in said shroud and rotationally supporting said forward end portion of said output shaft, said output shaft having a rear portion extending rearwardly from said rotor and rotatably mounted in a rear bearing, said rear bearing positioned rearwardly of said rotor and spaced from said rotor and secured in place by said grip, the rotor fixed to the output shaft forming a unitary assembly;
   an effector coaxial and integral with the output shaft at said distal forward end and operable to effect tissue modification during rotation of the output shaft and effector by the rotor; and
   an actuator operably coupled to the rotor and operable to selectively effect electrical energy transfer to the rotor to selectively effect rotation of the rotor,
   wherein the shroud includes a male threaded portion and the grip includes a nose with a female threaded portion, and wherein the shroud is configured to be secured to the nose by threaded engagement of the male threaded portion with the female threaded portion.

2. The surgical tool of claim 1, wherein the motor being an electric motor.

3. The surgical tool of claim 2, wherein the actuator includes a switch operably connected to an electrical conductor connected to the motor.

4. The surgical tool of claim 1, wherein the axis of rotation of the rotor and the effector being coaxial.

5. The surgical tool of claim 1, wherein said forward portion of said output shaft includes two or more said forward bearings, at least one of said forward bearings being mounted in said shroud and at least one of said forward bearings mounted in said grip.

6. The surgical tool of claim 1, wherein the tool is contained in a package, wherein the package has indicia indicating the type of said effector that is included as a portion of the output shaft.

7. The surgical tool of claim 1, wherein the grip includes an auxiliary handle.

8. A rotary surgical tool comprising:
   a grip adapted for holding with a hand;
   a shroud releasably coupled to the grip with a bayonet mount arrangement, wherein the grip includes a plurality of L-shaped recesses, each recess configured to receive one of a plurality of retainer pins on a sleeve of the shroud upon axial movement of the grip;
   a motor mounted in the grip, the motor including a rotor mounted for rotation within the motor;
   an output shaft extending through and rotationally supporting the rotor, said output shaft fixed to and axially aligned with the rotor forming a unitary assembly and at least partially carried by the shroud for rotation by the rotor, said output shaft having a distal end spaced from the rotor, the shroud carried by said grip and surrounding a forward end portion of said output shaft, and including at least one bearing mounted in said shroud and rotationally supporting said output shaft, said output shaft having a rear portion extending rearwardly from said rotor and rotatably mounted in a rear bearing, said rear bearing positioned rearwardly of said rotor and spaced from said rotor and supported and secured in place by said grip;
   an effector integral with the output shaft at said distal end and operable to effect tissue modification during rotation of the effector by the rotor; and
   an actuator operably coupled to the rotor and operable to selectively effect electrical energy transfer to the rotor to selectively effect rotation of the rotor.

9. The surgical tool of claim 1, wherein the shroud includes a shoulder at a proximal end of the shroud, wherein the shoulder is configured to engage a free end of the nose to limit how far the shroud can be threaded onto the nose.

* * * * *